United States Patent
George et al.

(10) Patent No.: US 9,578,872 B2
(45) Date of Patent: Feb. 28, 2017

(54) CO-CRYSTALS OF PYRIMETHANIL OR CYPRODINIL

(75) Inventors: Neil George, Bracknell (GB); James Owen Forrest, Bracknell (GB); Rebecca Claire Burton, Bracknell (GB); Christer Björn Aakeroy, Manhatten, KS (US)

(73) Assignee: Syngenta Limited, Guildford, Surrey (GB)

( * ) Notice: Subject to any disclaimer, the term of this patent is extended or adjusted under 35 U.S.C. 154(b) by 359 days.

(21) Appl. No.: 13/696,180

(22) PCT Filed: Apr. 6, 2011

(86) PCT No.: PCT/GB2011/000531
§ 371 (c)(1),
(2), (4) Date: Mar. 11, 2013

(87) PCT Pub. No.: WO2011/128618
PCT Pub. Date: Oct. 20, 2011

(65) Prior Publication Data
US 2013/0203792 A1    Aug. 8, 2013

(30) Foreign Application Priority Data
Apr. 15, 2010 (GB) .................................. 1006326.1

(51) Int. Cl.
*A01N 43/54* (2006.01)
*A61K 31/505* (2006.01)
*A01N 25/00* (2006.01)
*C07D 239/42* (2006.01)

(52) U.S. Cl.
CPC ............ *A01N 25/00* (2013.01); *A01N 43/54* (2013.01); *C07D 239/42* (2013.01)

(58) Field of Classification Search
None
See application file for complete search history.

(56) References Cited

FOREIGN PATENT DOCUMENTS

| EP | 0655441 | 5/1995 |
|---|---|---|
| GB | WO 2010038008 A2 * | 4/2010 |
| WO | 2008117060 | 10/2008 |
| WO | 2009047043 | 4/2009 |
| WO | 2010038008 | 4/2010 |

OTHER PUBLICATIONS

Hamilton, Darren G. et al: "A neutral donor-acceptor pi-stack: solid-state structures of 1:1 pyromellitic di imide-dialkoxynaphthalene cocrystals", Australian Journal of Chemistry, CSIRO, AU, vol. 50, No. 5, Jan. 1, 1997, pp. 439-445.
M L Highfill et al: "Superstructural Variety from an Alkylated Triazine: Formation of One-Dimensional Hydrogen-Bonded Arrays or Cyclic Rosettes", Crystal Growth & Design, vol. 2, No. 1, Nov. 28, 2001, pp. 15-20.
CB Aakeroy et al.: "Constructing, deconstructing, and reconstructing ternary supermolecules", Chem Comm, No. 38, Oct. 14, 2007, pp. 3936-3938.

* cited by examiner

*Primary Examiner* — Dennis Heyer
*Assistant Examiner* — Daniel M Podgorski
(74) *Attorney, Agent, or Firm* — R. Kody Jones

(57) ABSTRACT

The present invention relates to co-crystals of cyprodinil or pyrimethanil and a co-crystal forming compound which has at least one imide and/or oxime functional group.

17 Claims, 7 Drawing Sheets

CO-CRYSTALS OF PYRIMETHANIL OR CYPRODINIL

This application is a 371 of International Application No. PCT/GB2011/000531 filed Apr. 6, 2011, which claims priority to GB 1006326.1 filed Apr. 15, 2010, the contents of which are incorporated herein by reference.

The present invention relates to novel co-crystals of cyprodinil or pyrimethanil and to the use of the co-crystals in fungicidal compositions, in particular agrochemical compositions.

Both cyprodinil and pyrimethanil are anilinopyrimidine fungicides and are thought to act by inhibiting the biosynthesis of methionine and the secretion of fungal hydrolytic enzymes. Cyprodinil is used as a foliar fungicide on cereals, grapes, pome fruit, stone fruit, strawberries, vegetables, field crops and ornamentals and as a seed dressing on barley to control a wide range of pathogens such as *Tapesia yallundae* and *T. acuformis, Erysiphe* spp., *Pyrenophora teres, Rhynchosporium secalis, Botrytis* spp., *Alternaria* spp., *Venturia* spp. and *Monilinia* spp. Pyrimethanil is used to control grey mould (*Botrytis cinerea*) on vines, fruit, vegetables and ornamentals and in the control of leaf scab (*Venturia inaequalis* or *V. pirina*) on pome fruit. Both are available commercially and are described in The Pesticide Manual" [The Pesticide Manual—A World Compendium; Thirteenth Edition; Editor: C. D. S. Tomlin; The British Crop Protection Council].

Two polymorphic forms of cyprodinil are known to exist, both of which exhibit characteristic, but different, melting ranges: form A melts between 70 and 72° C. and form B between 74 and 76° C. The thermodynamic stability of polymorphic forms A and B is enantiotropically related and exhibits a phase transition temperature, which, although sensitive to other conditions, is typically at between 15 and 40° C.—certainly within the range of temperature fluctuations that may occur during the processing and storage of agrochemical formulations (typically from −10° C. to +50° C.). Below the phase transition temperature form A is the thermodynamically stable form and above the phase transition temperature, form B is the thermodynamically stable form. Therefore, under storage conditions a solid state of cyprodinil may undergo transformation by recrystallisation between the two polymorphic forms leading to the generation of large and undesirable particles, which could, for example, block spray nozzles during application of the product. In addition, such recrystallisation events mean that it may be difficult to maintain the product as a homogeneous formulation and this may lead to issues during transfer to dilution tanks and in ensuring the correct concentration on dilution. Accordingly, this behaviour currently limits the formulation of cyprodinil to compositions in which cyprodinil is solubilised (for example, emulsion concentrates). Similar issues exist with pyrimethanil, which may also crystallise under normal formulation and storage conditions. In addition, pyrimethanil is a rather volatile compound. These issues make formulation as, for example, a suspension concentrate, difficult and restrict the use of pyrimethanil in certain situations. As such, therefore, these issues mean that problems similar to those seen with cyprodinil occur during formulation, storage and application of pyrimethanil.

The formation of new solid states of cyprodinil or pyrimethanil which have at least one of the following properties: (i) do not exhibit phase transformation within the storage temperature fluctuation window; (ii) do not undergo crystallisation on formulation and storage; and (iii) are less volatile than the parent compound, would enable formulation as solid dispersions (for example, suspension concentrates, suspo-emulsions or wet granulations) which may have desirable toxicology, controlled release or chemical stability properties. In particular, it is noted that, in general, suspension concentrates may show lower phytotoxicity than emulsion concentrates, and, as such, these are clearly more desirable formulations for agrochemicals. Such characteristics may be due to the absence of solvents and other additives but, in addition, it is also possible that the co-crystal itself may show improved phytotoxicity when compared to the active ingredient alone.

Accordingly, the present invention provides novel co-crystalline forms of cyprodinil or pyrimethanil with improved properties as compared to the commercially available versions of these fungicides. In particular, it provides a co-crystal comprising an anilinopyrimidine fungicide selected from cyprodinil and pyrimethanil and a co-crystal forming compound which has at least one imide and/or oxime functional group. More particularly, the co-crystal forming compound is selected from the group consisting of pyromellitic diimide, terephthalaldehyde dioxime, dimethylglyoxime, 2,3-naphthalenedicarboximide, 2-hydroxyimino-2-phenylacetonitrile and phthalimide. Preferably, the anilinopyrimidine fungicide is cyprodinil.

The co-crystalline form of cyprodinil or pyrimethanil and the imide or oxime co-crystal forming compound may be characterised by a crystal morphology (described in terms of the unit cell) or by selected peaks of the powder X-ray diffraction pattern expressed in terms of 2 theta angles.

In one embodiment of the invention, there is provided a co-crystal form of cyprodinil and pyromellitic diimide. In a further embodiment, the co-crystal form of cyprodinil and pyromellitic diimide is characterised by the unit cell parameters of a cyprodinil/pyromellitic diimide single crystal shown in Table 1. This single crystal was obtained using the method of Example 1a. The stoichiometry of the co-crystal was confirmed as 2:1 by single crystal structure analysis.

TABLE 1

| Class | Monoclinic |
| --- | --- |
| Space Group | P2$_1$/c |
| Cell Lengths (Å) | a = 5.4584(9) |
|  | b = 17.189(3) |
|  | c = 16.918(3) |
| Cell Angles (°) | α = 90.00 |
|  | β = 94.973(6) |
|  | γ = 90.00 |
| Volume (Å$^3$) | 1581.35 |
| Z | 4 |
| R-factor (%) | 4.56 |

In the table, a, b, c = Length of the edges of the unit cell; α, β, γ = Angles of the unit cell; and Z = Number of cyprodinil:pyromellitic diimide complexes (2:1) in the unit cell.

In another embodiment, the co-crystal form of cyprodinil and pyromellitic diimide is characterised by a powder X-ray diffraction pattern expressed in terms of 2θ angles, wherein the powder X-ray diffraction pattern comprises at least three 2θ angle values selected from the group comprising 7.3±0.2, 10.5±0.2, 11.7±0.2, 18.3±0.2, 21.4±0.2, 26.8±0.2, 28.0±0.2, and 30.2±0.2. More preferably, the powder X-ray diffraction pattern comprises all of these 2θ angle values. These 2θ angle values are derived from those peaks of the powder X-ray diffraction pattern ascribable purely to the co-crystal; Table 2 comprises these 2θ values as well as values of further peaks which appear in the powder X-ray diffraction pattern of cyprodinil and/or pyromellitic diimide as well as the co-crystal. In one embodiment, the co-crystal form of cyprodinil and pyromellitic diimide is characterised by a powder X-ray diffraction pattern expressed in terms of 2θ angles, wherein the powder X-ray diffraction pattern comprise all the 2θ angle values listed in Table 2, that is, the powder X-ray diffraction pattern comprises 2θ angle values 7.3±0.2, 10.5±0.2, 11.7±0.2, 16.6±0.2, 17.1±0.2, 18.3±0.2, 18.8±0.2, 19.7±0.2, 21.4±0.2, 23.2±0.2, 24.1±0.2, 24.3±0.2, 26.4±0.2, 26.8±0.2, 28.0±0.2 and 30.2±0.2. All of the peaks in Table 2 are derived from a powder X-ray diffraction pattern that has been calculated using data from the cyrodinil-pyromellitic diimide single co-crystal obtained using the method of Example 1a. Table 2 also lists the intensity of these peaks (strong (S), medium (M) or weak (W)). The diffractogram from which all of these peak positions are derived is shown in FIG. 1.

TABLE 2

| Peak | 2θ | Intensity |
|---|---|---|
| 1 | 7.3 | S |
| 2 | 10.5 | W |
| 3 | 11.7 | S |
| 4 | 16.6 | M |
| 5 | 17.1 | M |
| 6 | 18.3 | W |
| 7 | 18.8 | M |
| 8 | 19.7 | W |
| 9 | 21.4 | M |
| 10 | 23.2 | W |
| 11 | 24.1 | M |
| 12 | 24.3 | M |
| 13 | 26.4 | M |
| 14 | 26.8 | S |
| 15 | 28.0 | M |
| 16 | 30.2 | M |

In another embodiment, the co-crystal form of cyprodinil and pyromellitic diimide is characterised by a powder X-ray diffraction pattern expressed in terms of 2θ angles, wherein the powder X-ray diffraction pattern comprises at least three 2θ angle values selected from the group comprising 7.2±0.2, 10.3±0.2, 11.5±0.2, 16.4±0.2, 16.7±0.2, 19.2±0.2, 20.1±0.2, 23.6±0.2 and 23.9±0.2. More preferably, the powder X-ray diffraction pattern comprises all of these 2θ angle values. These 2θ angle values are derived from those peaks of the powder X-ray diffraction pattern ascribable purely to the co-crystal; Table 3 comprises these 2θ values as well as values of further peaks which appear in the powder X-ray diffraction pattern of cyprodinil and/or pyromellitic diimide as well as the co-crystal. In one embodiment, the co-crystal form of cyprodinil and pyromellitic diimide is characterised by a powder X-ray diffraction pattern expressed in terms of 2θ angles, wherein the powder X-ray diffraction pattern comprise all the 2θangle values listed in Table 3, that is, the powder X-ray diffraction pattern comprises 274 angle values 7.2±0.2, 10.3±0.2, 11.5±0.2, 16.4±0.2, 16.7±0.2, 18.0±0.2, 18.5±0.2, 19.2±0.2, 20.1±0.2, 21.1±0.2, 23.0±0.2, 23.6±0.2, 23.9±0.2, 26.3±0.2, 27.5±0.2 and 29.5±0.2. All of the peaks in Table 3 are derived from a powder X-ray diffraction pattern of a cyprodinil-pyromellitic diimide co-crystal obtained using the method of Example 1a. Table 3 also lists the intensity of these peaks (strong (S), medium (M) or weak (W)). The diffractogram from which all of these peak positions are derived is shown in FIG. 2. Differential Scanning Calorimetry [DSC] data for the co-crystal are shown in FIG. 3.

TABLE 3

| Peak | 2θ | Intensity |
|---|---|---|
| 1 | 7.2 | S |
| 2 | 10.3 | W |
| 3 | 11.5 | S |
| 4 | 16.4 | M |
| 5 | 16.7 | W |
| 6 | 18.0 | W |
| 7 | 18.5 | M |
| 8 | 19.2 | W |
| 9 | 20.1 | W |
| 10 | 21.1 | M |
| 11 | 23.0 | W |
| 12 | 23.6 | M |
| 13 | 23.9 | W |
| 14 | 26.3 | S |
| 15 | 27.5 | M |
| 16 | 29.5 | M |

In one embodiment of the invention, there is provided a co-crystal form of cyprodinil and terephthalaldehyde dioxime. In a further embodiment, the co-crystal form of cyprodinil and terephthalaldehyde dioxime is characterised by the unit cell parameters of a cyprodinil/terephthalaldehyde dioxime single crystal shown in Table 4. This single crystal was obtained using the method of Example 1a. The stoichiometry of the co-crystal was confirmed as 2:1 by single crystal structure analysis.

TABLE 4

| Class | Monoclinic |
|---|---|
| Space Group | C 2/c |
| Cell Lengths (Å) | a = 40.859(3) |
|  | b = 5.0750(4) |
|  | c = 15.7686(11) |
| Cell Angles (°) | α = 90.00 |
|  | β = 100.4370(10) |
|  | γ = 90.00 |
| Volume (Å$^3$) | 3215.67 |
| Z | 8 |
| R-factor (%) | 3.88 |

In the table, a, b, c = Length of the edges of the unit cell; α, β, γ = Angles of the unit cell; and Z = Number of cyprodinil:terephthalaldehyde dioxime complexes (2:1) in the unit cell.

In another embodiment, the co-crystal form of cyprodinil and terephthalaldehyde dioxime is characterised by a powder X-ray diffraction pattern expressed in terms of 2θ angles, wherein the powder X-ray diffraction pattern comprises at least three 2θ angle values selected from the group comprising 4.4±0.2, 8.8±0.2, 11.4±0.2, 12.9±0.2, 17.7±0.2, 19.0±0.2, 19.2±0.2, 20.9±0.2, 24.4±0.2, 24.6±0.2, 25.7±0.2 and 28.7±0.2. More preferably, the powder X-ray diffraction pattern comprises all of these 2θ angle values. These 2θ angle values are derived from those peaks of the powder X-ray diffraction pattern ascribable purely to the co-crystal; Table 5 comprises these 2θ values as well as values of further peaks which appear in the powder X-ray diffraction pattern of cyprodinil and/or terephthalaldehyde dioxime as well as the co-crystal. In one embodiment, the co-crystal form of cyprodinil and terephthalaldehyde dioxime is characterised by a powder X-ray diffraction pattern expressed in terms of 2θ angles, wherein the powder X-ray diffraction pattern comprise all the 2θ angle values listed in Table 5, that is, the powder X-ray diffraction pattern comprises 2θ angle values 4.4±0.2, 8.8±0.2, 11.4±0.2, 12.9±0.2, 13.2±0.2, 17.7±0.2, 19.0±0.2, 19.2±0.2, 20.9±0.2, 21.3±0.2, 22.5±0.2, 23.0±0.2, 23.4±0.2, 24.4±0.2, 24.6±0.2, 25.7±0.2, 26.4±0.2 and 28.7±0.2. All of the peaks in Table 5 are derived from a powder X-ray diffraction pattern that has been calculated using data from the cyprodinil-terephthalaldehyde dioxime single co-crystal obtained using the method of Example 1a. Table 5 also lists the intensity of these peaks (strong (S), medium (M) or weak (W)). The diffractogram from which all of these peak positions are derived is shown in FIG. 4.

TABLE 5

| Peak | 2θ | Intensity |
|---|---|---|
| 1 | 4.4 | W |
| 2 | 8.8 | S |
| 3 | 11.4 | S |
| 4 | 12.9 | M |
| 5 | 13.2 | S |
| 6 | 17.7 | M |
| 7 | 19.0 | M |
| 8 | 19.2 | W |
| 9 | 20.9 | M |
| 10 | 21.3 | S |
| 11 | 22.5 | M |
| 12 | 23.0 | M |
| 13 | 23.4 | M |
| 14 | 24.4 | M |
| 15 | 24.6 | S |
| 16 | 25.7 | M |
| 17 | 26.4 | M |
| 18 | 28.7 | S |

In another embodiment, the co-crystal form of cyprodinil and terephthalaldehyde dioxime is characterised by a powder X-ray diffraction pattern expressed in terms of 2θ angles, wherein the powder X-ray diffraction pattern comprises at least three 2θ angle values selected from the group comprising 4.3±0.2, 8.9±0.2, 12.9±0.2, 17.6±0.2, 19.0±0.2, 19.3±0.2, 20.9±0.2, 22.3±0.2, 24.4±0.2 and 26.6±0.2. More preferably, the powder X-ray diffraction pattern comprises all of these 2θ angle values. These 2θ angle values are derived from those peaks of the powder X-ray diffraction pattern ascribable purely to the co-crystal; Table 6 comprises these 2θ values as well as values of further peaks which appear in the powder X-ray diffraction pattern of cyprodinil and/or terephthalaldehyde dioxime as well as the co-crystal. In one embodiment, the co-crystal form of cyprodinil and terephthalaldehyde dioxime is characterised by a powder X-ray diffraction pattern expressed in terms of 2θ angles, wherein the powder X-ray diffraction pattern comprise all the 2θ angle values listed in Table 6, that is, the powder X-ray diffraction pattern comprises 2θ angle values 4.3±0.2, 8.9±0.2, 11.4±0.2, 12.9±0.2, 13.2±0.2, 17.6±0.2, 19.0±0.2, 19.3±0.2, 20.9±0.2, 21.3±0.2, 22.3±0.2, 22.9±0.2, 24.4±0.2, 26.3 0.2, 26.6±0.2 and 28.4±0.2. All of the peaks in Table 6 are derived from a powder X-ray diffraction pattern of a cyprodinil-terephthalaldehyde dioxime co-crystal obtained using the method of Example 1a. Table 6 also lists the intensity of these peaks (strong (S), medium (M) or weak (W)). The diffractogram from which all of these peak positions are derived is shown in FIG. 5. Differential Scanning Calorimetry [DSC] data for the co-crystal are shown in FIG. 6.

TABLE 6

| Peak | 2θ | Intensity |
|---|---|---|
| 1 | 4.3 | W |
| 2 | 8.9 | S |
| 3 | 11.4 | S |
| 4 | 12.9 | M |
| 5 | 13.2 | S |

TABLE 6-continued

| Peak | 2θ | Intensity |
|---|---|---|
| 6 | 17.6 | M |
| 7 | 19.0 | M |
| 8 | 19.3 | W |
| 9 | 20.9 | M |
| 10 | 21.3 | S |
| 11 | 22.3 | M |
| 12 | 22.9 | M |
| 13 | 24.4 | S |
| 14 | 26.3 | M |
| 15 | 26.6 | M |
| 16 | 28.4 | S |

In one embodiment of the invention, there is provided a co-crystal form of cyprodinil and dimethylglyoxime. In a further embodiment, the co-crystal form of cyprodinil and dimethylglyoxime is characterised by the unit cell parameters of a cyprodinil/dimethylglyoxime single crystal shown in Table 7. This single crystal was obtained using the method of Example 1b. The stoichiometry of the co-crystal was confirmed as 2:1 by single crystal structure analysis.

TABLE 7

| Class | Orthorhombic |
|---|---|
| Space Group | P b c a |
| Cell Lengths (Å) | a = 7.7768(9) |
|  | b = 18.376(2) |
|  | c = 21.162(2) |
| Cell Angles (°) | α = 90.00 |
|  | β = 90.00 |
|  | γ = 90.00 |
| Volume (Å$^3$) | 3024.19 |
| Z | 8 |
| R-factor (%) | 7.39 |

In the table, a, b, c = Length of the edges of the unit cell; α, β, γ = Angles of the unit cell; and Z = Number of cyprodinil:dimethylglyoxime complexes (2:1) in the unit cell.

In another embodiment, the co-crystal form of cyprodinil and dimethylglyoxime is characterised by a powder X-ray diffraction pattern expressed in terms of 2θ angles, wherein the powder X-ray diffraction pattern comprises at least three 2θ angle values selected from the group comprising 8.4±0.2, 9.6±0.2, 10.5±0.2, 12.7±0.2, 13.0±0.2, 15.8±0.2, 18.9±0.2, 20.9±0.2, 25.8±0.2 and 31.4±0.2. More preferably, the powder X-ray diffraction pattern comprises all of these 2θ angle values. These 2θ angle values are derived from those peaks of the powder X-ray diffraction pattern ascribable purely to the co-crystal; Table 8 comprises these 2θ values as well as values of further peaks which appear in the powder X-ray diffraction pattern of cyprodinil and/or dimethylglyoxime as well as the co-crystal. In one embodiment, the co-crystal form of cyprodinil and dimethylglyoxime is characterised by a powder X-ray diffraction pattern expressed in terms of 2θ angles, wherein the powder X-ray diffraction pattern comprise all the 2θ angle values listed in Table 8, that is, the powder X-ray diffraction pattern comprises 2θ angle values 8.4±0.2, 9.6±0.2, 10.5±0.2, 12.7±0.2, 13.0±0.2, 15.0±0.2, 15.8±0.2, 17.1±0.2, 18.9±0.2, 20.3±0.2, 20.9±0.2, 22.4±0.2, 23.4±0.2, 25.3±0.2, 25.8±0.2, 27.5±0.2 and 31.4±0.2. All of the peaks in Table 8 are derived from a powder X-ray diffraction pattern that has been calculated using data from the cyprodinil-dimethylglyoxime single co-crystal obtained using the method of Example 1b. Table 8 also lists the intensity of these peaks (strong (S), medium (M) or weak (W)). The diffractogram from which all of these peak positions are derived is shown in FIG. 7.

TABLE 8

| Peak | 2θ | Intensity |
|---|---|---|
| 1 | 8.4 | W |
| 2 | 9.6 | S |
| 3 | 10.5 | S |
| 4 | 12.7 | W |
| 5 | 13.0 | S |
| 6 | 15.0 | W |
| 7 | 15.8 | M |
| 8 | 17.1 | W |
| 9 | 18.9 | M |
| 10 | 20.3 | W |
| 11 | 20.9 | W |
| 12 | 22.4 | M |
| 13 | 23.4 | S |
| 14 | 25.3 | M |
| 15 | 25.8 | W |
| 16 | 27.5 | M |
| 17 | 31.4 | W |

In another embodiment, the co-crystal form of cyprodinil and dimethylglyoxime is characterised by a powder X-ray diffraction pattern expressed in terms of 2θ angles, wherein the powder X-ray diffraction pattern comprises at least three 2θ angle values selected from the group comprising 8.3±0.2, 10.4±0.2, 12.8±0.2, 16.7±0.2, 16.9±0.2, 20.6±0.2, 22.2±0.2, 24.8±0.2, 25.6±0.2 and 30.9±0.2. More preferably, the powder X-ray diffraction pattern comprises all of these 2θ angle values. These 2θ angle values are derived from those peaks of the powder X-ray diffraction pattern ascribable purely to the co-crystal; Table 9 comprises these 2θ values as well as values of further peaks which appear in the powder X-ray diffraction pattern of cyprodinil and/or dimethylglyoxime as well as the co-crystal. In one embodiment, the co-crystal form of cyprodinil and dimethylglyoxime is characterised by a powder X-ray diffraction pattern expressed in terms of 2θ angles, wherein the powder X-ray diffraction pattern comprise all the 2θ angle values listed in Table 9, that is, the powder X-ray diffraction pattern comprises 2θ angle values 8.3±0.2, 9.5±0.2, 10.4±0.2, 12.8±0.2, 14.7±0.2, 15.7±0.2, 16.7±0.2, 16.9±0.2, 18.7±0.2, 19.3±0.2, 20.0±0.2, 20.6±0.2, 22.2±0.2, 23.0±0.2, 24.8±0.2, 25.6±0.2, 27.1±0.2 and 30.9±0.2. All of the peaks in Table 9 are derived from a powder X-ray diffraction pattern of a cyprodinil-dimethylglyoxime co-crystal obtained using the method of Example 1b. Table 9 also lists the intensity of these peaks (strong (S), medium (M) or weak (W)). The diffractogram from which all of these peak positions are derived is shown in FIG. 8. Differential Scanning Calorimetry [DSC] data for the co-crystal are shown in FIG. 9.

TABLE 9

| Peak | 2θ | Intensity |
|---|---|---|
| 1 | 8.3 | S |
| 2 | 9.5 | W |
| 3 | 10.4 | M |
| 4 | 12.8 | M |
| 5 | 14.7 | M |
| 6 | 15.7 | M |
| 7 | 16.7 | M |
| 8 | 16.9 | W |
| 9 | 18.7 | W |
| 10 | 19.3 | W |
| 11 | 20.0 | M |
| 12 | 20.6 | M |
| 13 | 22.2 | S |
| 14 | 23.0 | S |
| 15 | 24.8 | M |
| 16 | 25.6 | M |

TABLE 9-continued

| Peak | 2θ | Intensity |
|---|---|---|
| 17 | 27.1 | W |
| 18 | 30.9 | W |

In one embodiment of the invention, there is provided a co-crystal form of cyprodinil and 2,3-naphthalenedicarboximide. In a further embodiment, the co-crystal form of cyprodinil and 2,3-naphthalenedicarboximide is characterised by the unit cell parameters of a cyprodinil/2,3-naphthalenedicarboximide single crystal shown in Table 10. This single crystal was obtained using the method of Example 1d. The stoichiometry of the co-crystal was confirmed as 1:1 by single crystal structure analysis.

TABLE 10

| Class | Monoclinic |
|---|---|
| Space Group | C 2/c |
| Cell Lengths (Å) | a = 48.549(8) |
|  | b = 5.6000(9) |
|  | c = 16.205(3) |
| Cell Angles (°) | α = 90.00 |
|  | β = 107.122(2) |
|  | γ = 90.00 |
| Volume (Å$^3$) | 4210.46 |
| Z | 8 |
| R-factor (%) | 4.38 |

In the table, a, b, c = Length of the edges of the unit cell; α, β, γ = Angles of the unit cell; and Z = Number of cyprodinil:2,3-naphthalenedicarboximide complexes (2:1) in the unit cell.

In another embodiment, the co-crystal form of cyprodinil and 2,3-naphthalenedicarboximide is characterised by a powder X-ray diffraction pattern expressed in terms of 2θ angles, wherein the powder X-ray diffraction pattern comprises at least three 2θ angle values selected from the group comprising 15.3±0.2, 16.0±0.2, 19.2±0.2, 21.3±0.2, 22.0±0.2, 23.9±0.2, 24.4±0.2 and 25.4±0.2. More preferably, the powder X-ray diffraction pattern comprises all of these 2θ angle values. These 2θ angle values are derived from those peaks of the powder X-ray diffraction pattern ascribable purely to the co-crystal; Table 11 comprises these 2θ values as well as values of further peaks which appear in the powder X-ray diffraction pattern of cyprodinil and/or 2,3-naphthalenedicarboximide as well as the co-crystal. In one embodiment, the co-crystal form of cyprodinil and 2,3-naphthalenedicarboximide is characterised by a powder X-ray diffraction pattern expressed in terms of 2θ angles, wherein the powder X-ray diffraction pattern comprise all the 2θ angle values listed in Table 11, that is, the powder X-ray diffraction pattern comprises 2θ angle values 11.5±0.2, 15.3±0.2, 16.0±0.2, 17.3±0.2, 19.2±0.2, 19.3±0.2, 19.9±0.2, 21.3±0.2, 22.0±0.2, 22.4±0.2, 22.9±0.2, 23.9±0.2, 24.4±0.2, 25.4±0.2, 27.2±0.2 and 27.9±0.2. All of the peaks in Table 11 are derived from a powder X-ray diffraction pattern that has been calculated using data from the cyprodinil-2,3-naphthalenedicarboximide single co-crystal obtained using the method of Example 1d. Table 11 also lists the intensity of these peaks (strong (S), medium (M) or weak (W)). The diffractogram from which all of these peak positions are derived is shown in FIG. 10.

TABLE 11

| Peak | 2θ | Intensity |
|---|---|---|
| 1 | 11.5 | S |
| 2 | 15.3 | W |

TABLE 11-continued

| Peak | 2θ | Intensity |
| --- | --- | --- |
| 3 | 16.0 | W |
| 4 | 17.3 | M |
| 5 | 19.2 | M |
| 6 | 19.3 | M |
| 7 | 19.9 | W |
| 8 | 21.3 | M |
| 9 | 22.0 | M |
| 10 | 22.4 | M |
| 11 | 22.9 | S |
| 12 | 23.9 | M |
| 13 | 24.4 | W |
| 14 | 25.4 | M |
| 15 | 27.2 | S |
| 16 | 27.9 | W |

In one embodiment of the invention, there is provided a co-crystal form of cyprodinil and 2-hydroxyimino-2-phenylacetonitrile. In a further embodiment, the co-crystal form of cyprodinil and 2-hydroxyimino-2-phenylacetonitrile is characterised by a powder X-ray diffraction pattern expressed in terms of 2θ angles, wherein the powder X-ray diffraction pattern comprises at least three 2θ angle values selected from the group comprising 7.5±0.2, 10.7±0.2, 13.8±0.2, 19.1±0.2, 21.4±0.2, 23.8±0.2, 27.7±0.2 and 30.9±0.2. More preferably, the powder X-ray diffraction pattern comprises all of these 2θ angle values. These 2θ angle values are derived from those peaks of the powder X-ray diffraction pattern ascribable purely to the co-crystal; Table 12 comprises these 2θ values as well as values of further peaks which appear in the powder X-ray diffraction pattern of cyprodinil and/or 2-hydroxyimino-2-phenylacetonitrile as well as the co-crystal. In one embodiment, the co-crystal form of cyprodinil and 2-hydroxyimino-2-phenylacetonitrile is characterised by a powder X-ray diffraction pattern expressed in terms of 2θ angles, wherein the powder X-ray diffraction pattern comprise all the 2θ angle values listed in Table 12, that is, the powder X-ray diffraction pattern comprises 2θ angle values 7.5±0.2, 10.7±0.2, 13.8±0.2, 15.6±0.2, 17.1±0.2, 18.6±0.2, 19.1±0.2, 19.9±0.2, 21.4±0.2, 22.5±0.2, 23.8±0.2, 24.3±0.2, 25.4±0.2, 27.7±0.2, 28.3±0.2, 29.3±0.2, 30.9±0.2 and 32.3±0.2. All of the peaks in Table 12 are derived from a powder X-ray diffraction pattern of a cyprodinil-2-hydroxyimino-2-phenylacetonitrile co-crystal obtained using the method of Example 1a. Table 12 also lists the intensity of these peaks (strong (S), medium (M) or weak (W)). The diffractogram from which all of these peak positions are derived is shown in FIG. 11. Differential Scanning Calorimetry [DSC] data for the co-crystal are shown in FIG. 12.

TABLE 12

| Peak | 2θ | Intensity |
| --- | --- | --- |
| 1 | 7.5 | M |
| 2 | 10.7 | M |
| 3 | 13.8 | M |
| 4 | 15.6 | M |
| 5 | 17.1 | M |
| 6 | 18.6 | W |
| 7 | 19.1 | S |
| 8 | 19.9 | S |
| 9 | 21.4 | S |
| 10 | 22.5 | M |
| 11 | 23.8 | M |
| 12 | 24.3 | S |
| 13 | 25.4 | M |
| 14 | 27.7 | W |

TABLE 12-continued

| Peak | 2θ | Intensity |
| --- | --- | --- |
| 15 | 28.3 | W |
| 16 | 29.3 | M |
| 17 | 30.9 | W |
| 18 | 32.3 | W |

In one embodiment of the invention, there is provided a co-crystal form of cyprodinil and phthalimide. In a further embodiment, the co-crystal form of cyprodinil and phthalimide is characterised by a powder X-ray diffraction pattern expressed in terms of 2θ angles, wherein the powder X-ray diffraction pattern comprises at least three 2θ angle values selected from the group comprising 7.6±0.2, 11.9±0.2, 13.7±0.2, 19.0±0.2, 20.6±0.2, 21.3±0.2, 22.2±0.2, 24.2±0.2, 24.5±0.2 and 25.5±0.2. More preferably, the powder X-ray diffraction pattern comprises all of these 2θ angle values. These 2θ angle values are derived from those peaks of the powder X-ray diffraction pattern ascribable purely to the co-crystal; Table 13 comprises these 2θ values as well as values of further peaks which appear in the powder X-ray diffraction pattern of cyprodinil and/or phthalimide as well as the co-crystal. In one embodiment, the co-crystal form of cyprodinil and phthalimide is characterised by a powder X-ray diffraction pattern expressed in terms of 2θ angles, wherein the powder X-ray diffraction pattern comprise all the 2θ angle values listed in Table 13, that is, the powder X-ray diffraction pattern comprises 2θ angle values 7.6±0.2, 9.5±0.2, 11.9±0.2, 13.7±0.2, 15.6±0.2, 17.7±0.2, 19.0±0.2, 19.4±0.2, 20.6±0.2, 21.3±0.2, 22.2±0.2, 22.9±0.2, 23.7±0.2, 24.2±0.2, 24.5±0.2, 25.5±0.2, 26.4±0.2 and 27.1±0.2. All of the peaks in Table 13 are derived from a powder X-ray diffraction pattern of a cyprodinil-phthalimide co-crystal obtained using the method of Example 1c. Table 13 also lists the intensity of these peaks (strong (S), medium (M) or weak (W)). The diffractogram from which all of these peak positions are derived is shown in FIG. 13. Differential Scanning Calorimetry [DSC] data for the co-crystal are shown in FIG. 14.

TABLE 13

| Peak | 2θ | Intensity |
| --- | --- | --- |
| 1 | 7.6 | M |
| 2 | 9.5 | S |
| 3 | 11.9 | W |
| 4 | 13.7 | M |
| 5 | 15.6 | S |
| 6 | 17.7 | W |
| 7 | 19.0 | M |
| 8 | 19.4 | W |
| 9 | 20.6 | M |
| 10 | 21.3 | M |
| 11 | 22.2 | M |
| 12 | 22.9 | W |
| 13 | 23.7 | S |
| 14 | 24.2 | M |
| 15 | 24.5 | M |
| 16 | 25.5 | W |
| 17 | 26.4 | M |
| 18 | 27.1 | S |

The co-crystals of the present invention are formed by contacting the cyprodinil or pyrimethanil with the co-crystal forming compound. This may be done by (i) grinding two solids together; (ii) melting one or both components and allowing them to recrystallise; and (iiia) solubilising, or partially solubilising, the cyprodinil or pyrimethanil and adding the co-crystal forming compound or (iiib) solubilising, or partially solubilising, the co-crystal forming compound and adding the cyprodinil or pyrimethanil. It may also be possible to solubilise, or partially solubilise, the cyprodinil or pyrimethanil in the co-crystal forming compound and vice versa. Crystallisation is then allowed to occur under suitable conditions. For example, crystallisation may require alteration of a property of the solutions, such as pH or temperature and may require concentration of solute, usually by removal of the solvent and typically by drying the solution. Solvent removal results in the concentration of cyprodinil or pyrimethanil increasing over time so as to facilitate crystallisation. In some cases, microwave irradiation or sonication (or both microwave irradiation and sonication) may be used to facilitate crystallisation. Once the solid phase comprising any crystals is formed, it may be tested as described herein.

Accordingly, the present invention provides a process for the production of a co-crystal of the invention comprising
(a) grinding, heating or contacting in solution the cyprodinil or pyrimethanil with the co-crystal forming compound, under crystallisation conditions so as to form a solid phase;
(b) isolating co-crystals comprising the cyprodinil or pyrimethanil and the co-crystal forming compound.

The co-crystal forming compound for use in the process of the invention is as defined above. In one embodiment of the process, the co-crystal forming compound has at least one imide and/or oxime functional group. In a further embodiment, the co-crystal forming compound is selected from the group consisting of pyromellitic diimide, terephthalaldehyde dioxime, dimethylglyoxime, 2,3-naphthalenedicarboximide, 2-hydroxyimino-2-phenylacetonitrile and phthalimide.

More suitably, the present invention provides a co-crystal of cyprodinil with a co-crystal forming compound as defined above.

As used herein 'co-crystal' means a crystalline material which comprises two or more unique components in a stoichiometric ratio each containing distinctive physical characteristics such as structure, melting point and heat of fusion. As used herein, a co-crystal is distinct from a crystalline salt as it consists of neutral components and not charged components as would be found in a salt. The co-crystal can be constructed through several modes of molecular recognition including hydrogen-bonding, Π (pi)-stacking, guest-host complexation and Van-Der-Waals interactions. Of the interactions listed above, hydrogen-bonding is the dominant interaction in the formation of the co-crystal, whereby a non-covalent bond is formed between a hydrogen bond donor of one of the moieties and a hydrogen bond acceptor of the other. Preferred co-crystals of the present invention are those where hydrogen bonding occurs between the co-crystal forming compound and the cyprodinil or pyrimethanil. It is noted that multi-point contacts may be formed in the crystal. For example, two molecules of cyprodinil may form contacts with different functional groups on the same co-crystal forming molecule, or, indeed, there may be multi-point contacts between a single molecule of cyprodinil and a single co-crystal forming molecul.

It is noted that hydrogen bonding can result in several different intermolecular assemblies and, as such, the co-crystals of the present invention may exist in one or more polymorphic forms. A polymorphic co-crystal may contain any molar ratio of cyprodinil to co-crystal forming compound, but typically will be in the range of from 5:1 to 1:5. In systems where the cyprodinil or the co-crystal forming compound exhibit isomerism, a polymorphic form may also contain a different isomeric ratio. Each polymorphic form may be defined by one or more solid state analytical techniques including single crystal X-ray diffraction, powder X-ray diffraction, DSC, Raman or infra-red spectroscopy.

Suitably, the molar ratio of cyprodinil or pyrimethanil to co-crystal forming compound in the co-crystal is in the range of from 5:1 to 1:5. More suitably, the molar ratio of cyprodinil or pyrimethanil to co-crystal forming compound in the co-crystal is in the range of from 3:1 to 1:3. Even more suitably, the molar ratio of cyprodinil or pyrimethanil to co-crystal forming compound is in the range of 2:1 to 1:1.

Assaying the solid phase for the presence of co-crystals of the cyprodinil or pyrimethanil and the co-crystal forming compound may be carried out by conventional methods known in the art. For example, it is convenient and routine to use powder X-ray diffraction techniques to assess the presence of the co-crystals. This may be effected by comparing the spectra of cyprodinil or pyrimethanil, the co-crystal forming compound and putative co-crystals in order to establish whether or not true co-crystals have been formed. Other techniques used in an analogous fashion, include differential scanning calorimetry (DSC), thermogravimetric analysis (TGA) and Raman or Infra-red spectroscopy, NMR, gas chromatography or HPLC. Single crystal X-ray diffraction is especially useful in identifying co-crystal structures.

The co-crystals of the invention may be readily incorporated into fungicidal compositions (including agrochemical compositions) by conventional means. Accordingly, the invention also provides a fungicidal composition comprising a fungicidally effective amount of a co-crystal of the invention as defined above and a diluent. In one embodiment, the fungicidal composition is an agrochemical composition. The agrochemical compositions comprising the co-crystals of the present invention can be used for the control of plant pathogenic fungi on a number of plant species. Accordingly, the invention also provides a method of preventing or controlling fungal infection on plants or plant propagation material comprising treating the plant or plant propagation material with a fungicidally effective amount of an agricultural composition of the invention. By 'plant propagation material' is meant seeds of all kinds (fruit, tubers, bulbs, grains etc.), cuttings, cut shoots and the like.

In particular, the agrochemical compositions of the invention can be used to control, for example, *Cochliobolus sativus, Erysiphe* spp. including *E. graminis, Leptosphaeria nodorum, Puccinia* spp., *Pyrenophora teres, Pyrenophora tritici-repentis, Rhynchosporium secalis, Septoria* spp, *Mycosphaerella musicola, Mycosphaerella fijiensis* var. *difformis, Sclerotinia homoeocarpa, Rhizoctonia solani, Helminthosporium* spp. including *Helminthosporium oryzae*, dirty panicle complex, *Hemileia vastatrix, Cercospora* spp., *Monilinia* spp., *Podosphaera* spp., *Sphaerotheca* spp., *Tranzschelia* spp., *Tapesia yallundae* and *T. acuformis, Botrytis* spp., *Alternaria* spp. and *Venturia* spp.

The agrochemical compositions of the present invention are suitable for controlling such disease on a number of plants and their propagation material including, but not limited to the following target crops: cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, but not limited to, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. *commutata* Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia* Willd), St. Augustinegrass (*Stenotaphrum secundatum* (Walt.) Kuntze); and centipedegrass (*Eremochloa ophiuroides* (Munro.) Hack.)).

In addition 'crops' are to be understood to include those crops that have been made tolerant to pests and pesticides, including herbicides or classes of herbicides, as a result of conventional methods of breeding or genetic engineering. Tolerance to e.g. herbicides means a reduced susceptibility to damage caused by a particular herbicide compared to conventional crop breeds. Crops can be modified or bred so as to be tolerant, for example, to HPPD inhibitors such as mesotrione or EPSPS inhibitors such as glyphosate.

The rate at which the agrochemical composition of the invention is applied will depend upon the particular type of fungus to be controlled, the degree of control required and the timing and method of application and can be readily determined by the person skilled in the art. In general, the compositions of the invention can be applied at an application rate of between 0.005 kilograms/hectare (kg/ha) and about 5.0 kg/ha, based on the total amount of active fungicide in the composition. An application rate of between about 0.1 kg/ha and about 1.5 kg/ha is preferred, with an application rate of between about 0.3 kg/ha and 0.8 kg/ha being especially preferred.

In practice, the agrochemical compositions comprising the co-crystals of the invention are applied as a formulation containing the various adjuvants and carriers known to or used in the industry. They may thus be formulated as granules, as wettable powders, as emulsifiable concentrates, as suspension concentrates (including oil dispersions), as powders or dusts, as flowables, as solutions, as suspensions or emulsions, suspo-emulsions or as controlled release forms such as microcapsules. Suitably, the agrochemical composition of the invention may be formulated as a suspension concentrate, a suspo-emulsion or a wet granulation. These formulations are described in more detail below and may contain as little as about 0.5% to as much as about 95% or more by weight of the active ingredient in the form of the co-crystal. The optimum amount will depend on formulation, application equipment and nature of the plant pathogenic fungi to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain by weight about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient by weight may range from about 0.5% to about 95% of the concentrate.

Suspension concentrates are formulations in which finely divided solid particles of the active compound are stably suspended. The solid particles may be suspended in an aqueous solution or in an oil (as an oil dispersion). Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient by weight may range from about 0.5% to about 95% of the concentrate.

Granular formulations include both extrudates and relatively coarse particles and may be applied without dilution to the area in which control of plant pathogenic fungi is required or dispersed in a spray tank before application, for example. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations for use without dilution normally contain by weight about 5% to about 25% active ingredients which may include surface-active agents such as heavy aromatic naphthas, kerosene and other petroleum fractions, or vegetable oils; and/or stickers such as dextrins, glue or synthetic resins. When the granules are to be dispersed in a spray tank before application, the active ingredient content by weight may be increased up to 80%.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically from about 1 to about 50 microns in diameter. The enclosed liquid typically constitutes about 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre (and preferably from 1 to 2 millimetres) in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Many of the formulations described above include wetting, dispersing or emulsifying agents. Examples are alkyl and alkylaryl sulphonates and sulphates and their salts, polyhydric alcohols; polyethoxylated alcohols, esters and fatty amines. These agents, when used, normally comprise from 0.1% to 40% by weight of the formulation.

Suitable agricultural adjuvants and carriers that are useful in formulating the compositions of the invention in the formulation types described above are well known to those skilled in the art. Suitable examples of the different classes are found in the non-limiting list below.

Liquid carriers that can be employed include water and any solvents in which the co-crystal has no or limited solubility e.g. toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulphonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. The surface-active agents can be anionic, cationic, non-ionic or polymeric in character and can be employed as emulsifying agents, wetting agents, suspending agents or for other purposes. Typical surface active agents include salts of alkyl sulphates, such as diethanolammonium lauryl sulphate; alkylarylsulphonate salts, such as calcium dodecylbenzenesulphonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulphonate salts, such as sodium dibutylnaphthalenesulphonate; dialkyl esters of sulphosuccinate salts, such as sodium di(2-ethylhexyl)sulphosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like.

In addition, further, other biocidally active ingredients or compositions may be combined with the agrochemical composition of this invention. For example, the compositions may contain other fungicides, herbicides, insecticides, bactericides, acaricides, nematicides and/or plant growth regulators, in order to broaden the spectrum of activity.

Each of the above formulations can be prepared as a package containing the fungicides together with other ingredients of the formulation (diluents, emulsifiers, to surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of power-dusters, broom and hand sprayers and spray dusters. The formulations can also be applied from airplanes as a dust or a spray or by rope wick applications. Both solid and liquid formulations may also be applied to the soil in the locus of the plant to be treated allowing the active ingredient to penetrate the plant through the roots. The formulations of the invention may also be used for dressing applications on plant propagation material to provide protection against fungus infections on the plant propagation material as well as against phytopathogenic fungi occurring in the soil. Suitably, the active ingredient may be applied to plant propagation material to be protected by impregnating the plant propagation material, in particular, seeds, either with a liquid formulation of the fungicide or coating it with a solid formulation. In special cases, other types of application are also possible, for example, the specific treatment of plant cuttings or twigs serving propagation.

Suitably, the agrochemical compositions and formulations of the present invention are applied prior to disease development. Rates and frequency of use of the formulations are those conventionally used in the art and will depend on the risk of infestation by the fungal pathogen.

The present invention will now be described by way of the following non-limiting examples and figures, wherein.

EXAMPLES

Figure 1:
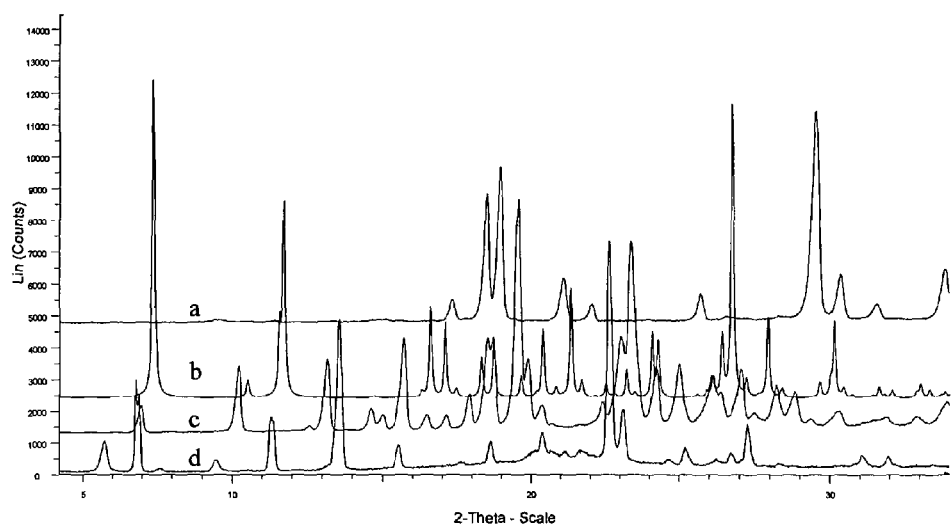
FIG. 1 shows the powder X-Ray diffraction patterns (a) of pyromellitic diimide, (b) calculated from single crystal data from a co-crystal of cyprodinil and pyromellitic diimide obtained using the techniques described in Example 1a, (c) cyprodinil form A and (d) cyprodinil form B.
Figure 2:
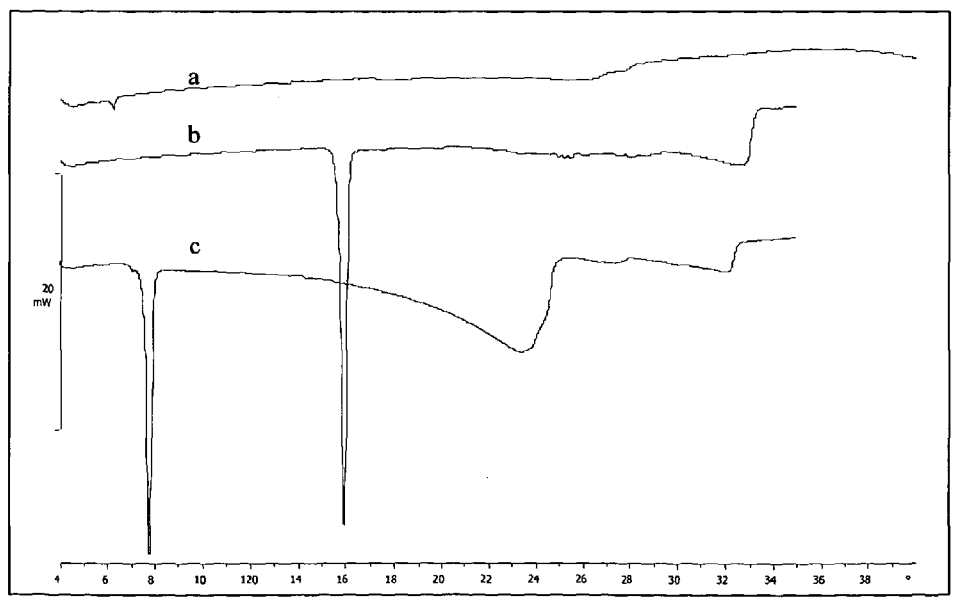
FIG. 2 shows the powder X-Ray diffraction patterns of (a) pyromellitic diimide, (b) cyprodinil-pyromellitic diimide co-crystal obtained using the technique described in Example 1a, (c) cyprodinil form A and (d) cyprodinil form B.
Figure 3:
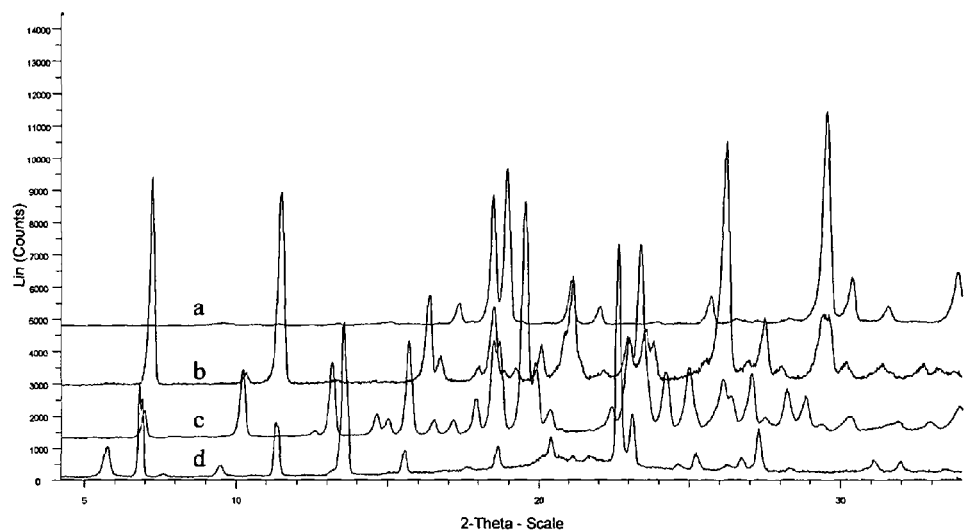
FIG. 3 shows the DSC trace of (a) pyromellitic diimide, (b) cyprodinil-pyromellitic diimide co-crystal obtained using the technique described in Example 1a and (c) cyprodinil form B.
Figure 4:
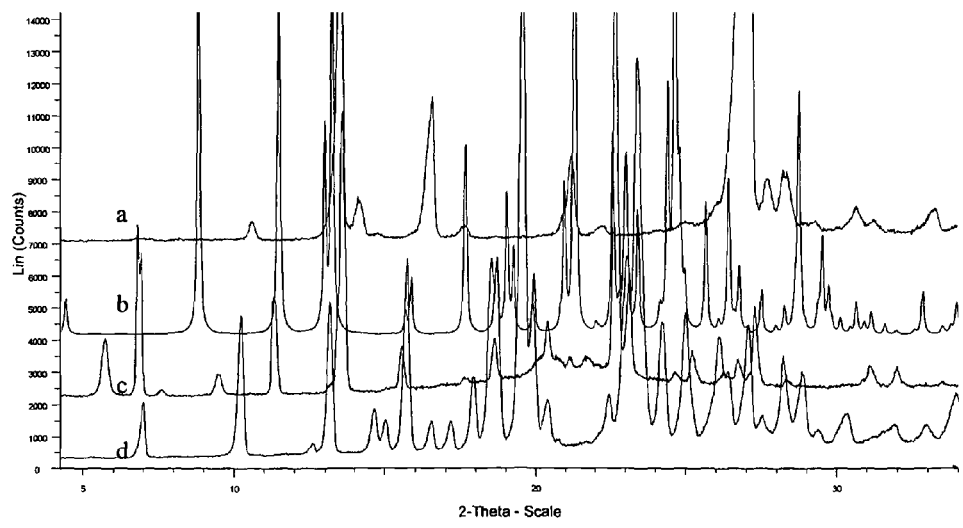
FIG. 4 shows the powder X-Ray diffraction patterns (a) of terephthalaldehyde dioxime, (b) calculated from single crystal data from a co-crystal of cyprodinil and terephthalaldehyde dioxime obtained using the technique described in Example 1a, (c) cyprodinil form A and (d) cyprodinil form B.
Figure 5:
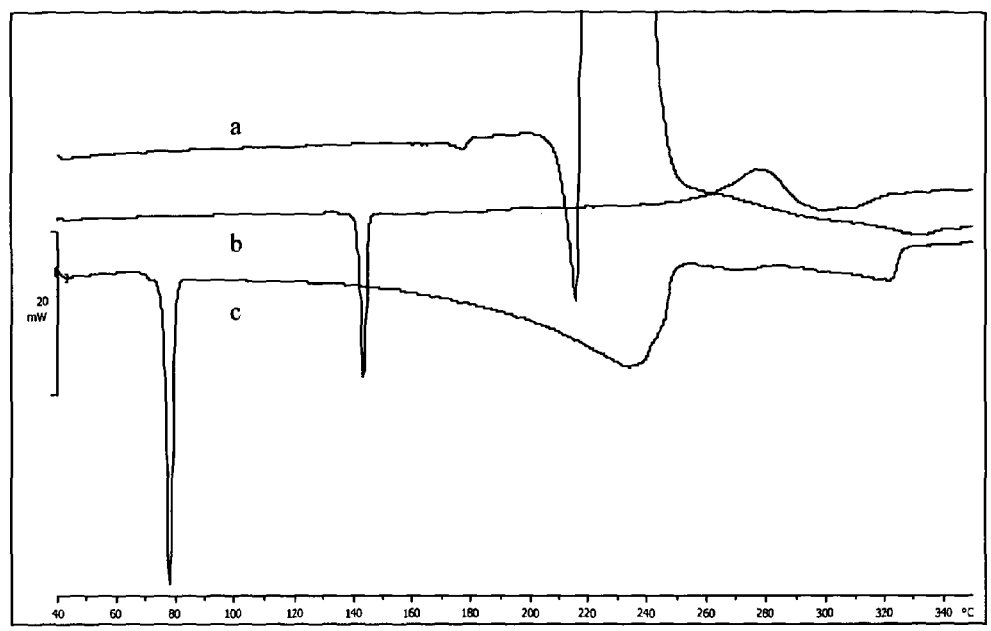
FIG. 5 shows the powder X-Ray diffraction patterns of (a) terephthalaldehyde dioxime (b) cyprodinil-terephthalaldehyde dioxime co-crystal obtained using the technique described in Example 1 a, (c) cyprodinil form A and (d) cyprodinil form B.
Figure 6:
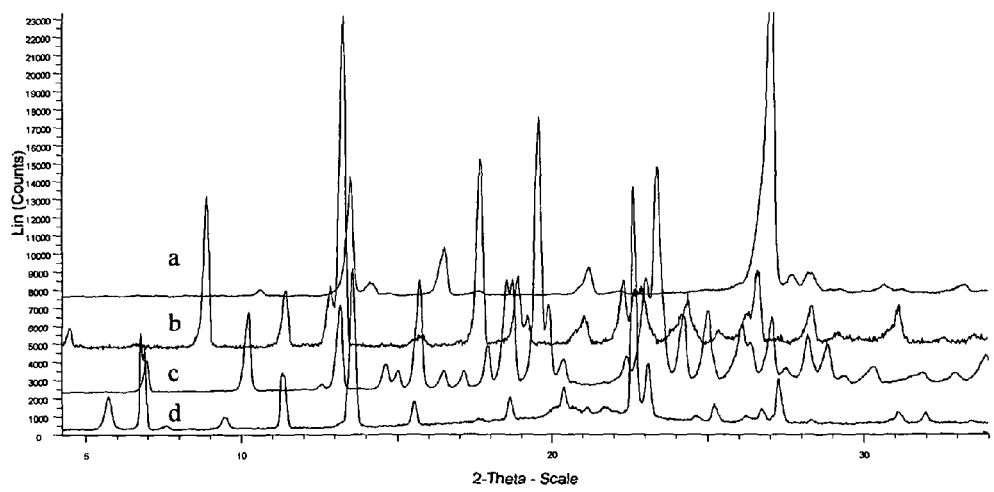
FIG. 6 shows the DSC shows the DSC traces of (a) terephthalaldehyde dioxime (b) cyprodinil-terephthalaldehyde dioxime co-crystal obtained using the technique described in Example 1a and (c) Cyprodinil form B.
Figure 7:
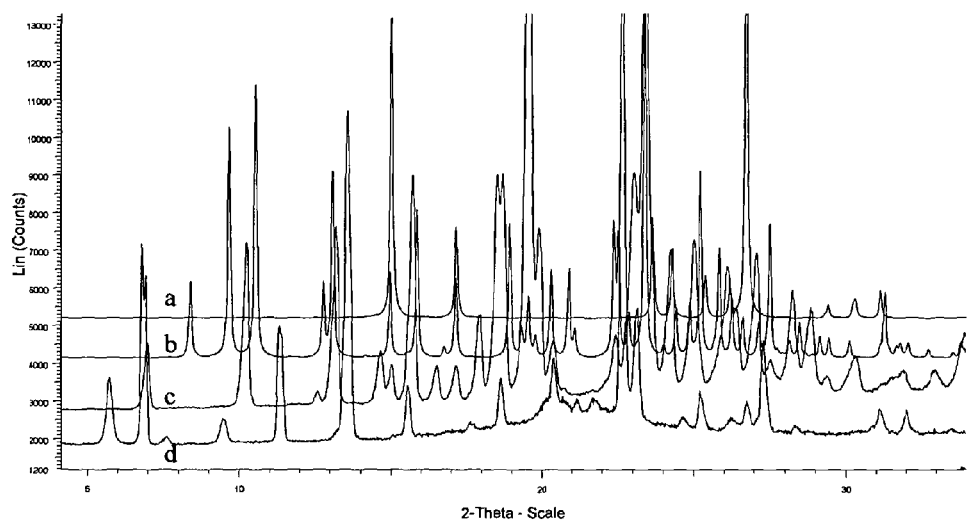
FIG. 7 shows the powder X-Ray diffraction patterns (a) of dimethylglyoximem, (b) calculated from single crystal data from a co-crystal of cyprodinil and dimethylglyoxime obtained using the technique described in Example 1 b, (c) cyprodinil form A and (d) cyprodinil form B.
Figure 8:
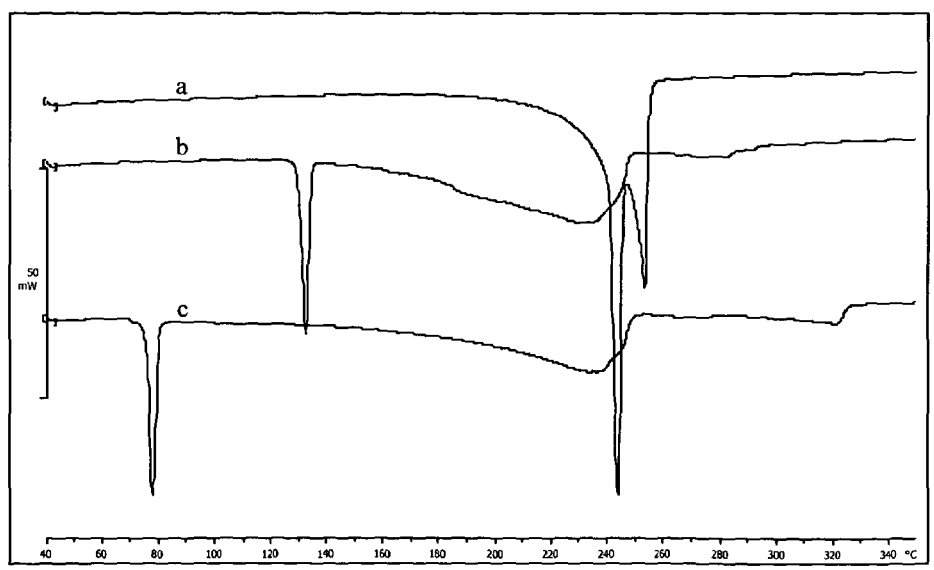
FIG. 8 shows the powder X-Ray diffraction patterns of (a) dimethylglyoxime, (b) cyprodinil-dimethylglyoxime co-crystal obtained using the technique described in Example 1 b, (c) cyprodinil form A and (d) cyprodinil form B.
Figure 9:
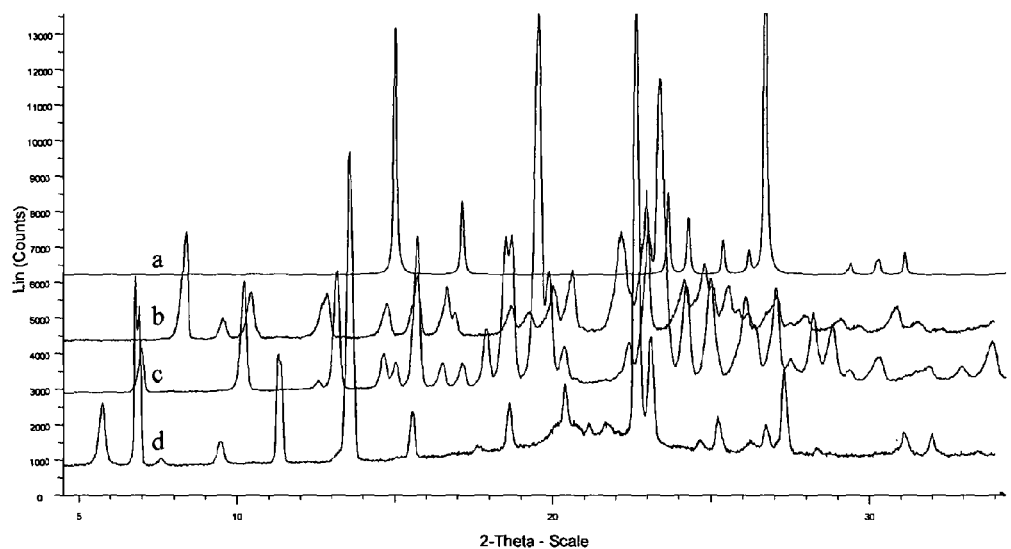
FIG. 9 shows the DSC traces of (a) dimethylglyoxime (b) cyprodinil-dimethylglyoxime co-crystal obtained using the technique described in Example 1b and (c) cyprodinil form B.
Figure 10:
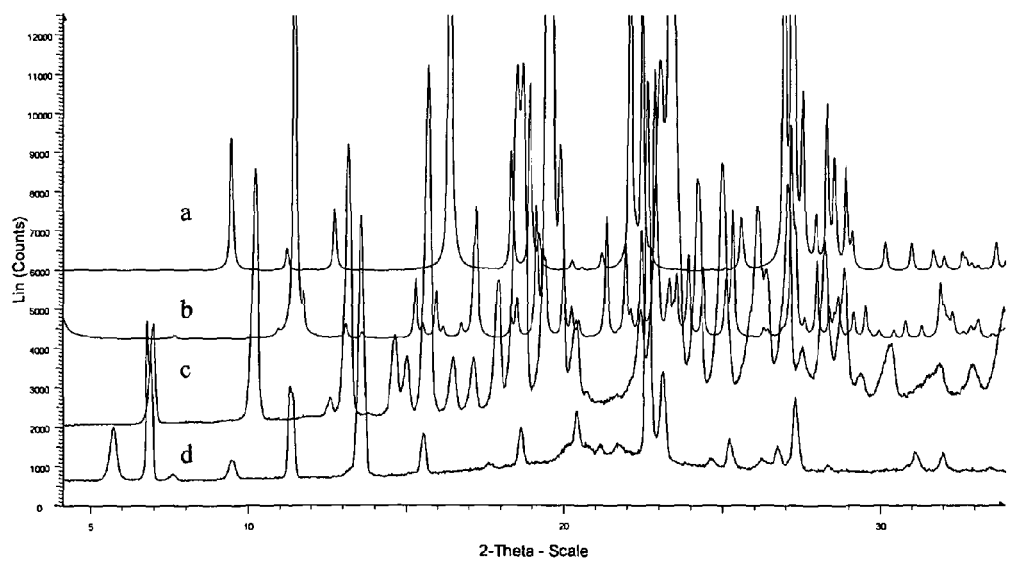
FIG. 10 shows the powder X-Ray diffraction patterns (a) of 2,3-naphthalenedicarboximide (b) calculated from single crystal data from a co-crystal of cyprodinil and 2,3-naphthalenedicarboximide obtained using the technique described in Example 1d, (c) cyprodinil form A and (d) cyprodinil form B.
Figure 11:
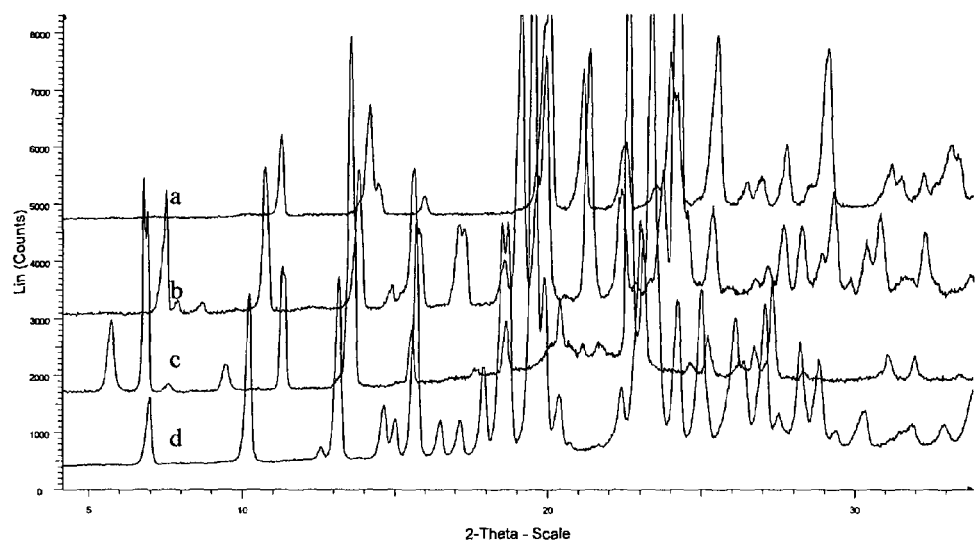
FIG. 11 shows the powder X-Ray diffraction patterns of (a) 2-hydroxyimino-2-phenylacetonitrile, (b) cyprodinil-2-hydroxyimino-2-phenylacetonitrile co-crystal obtained using the technique described in Example 1a, (c) cyprodinil form A and (d) cyprodinil form B.
Figure 12:
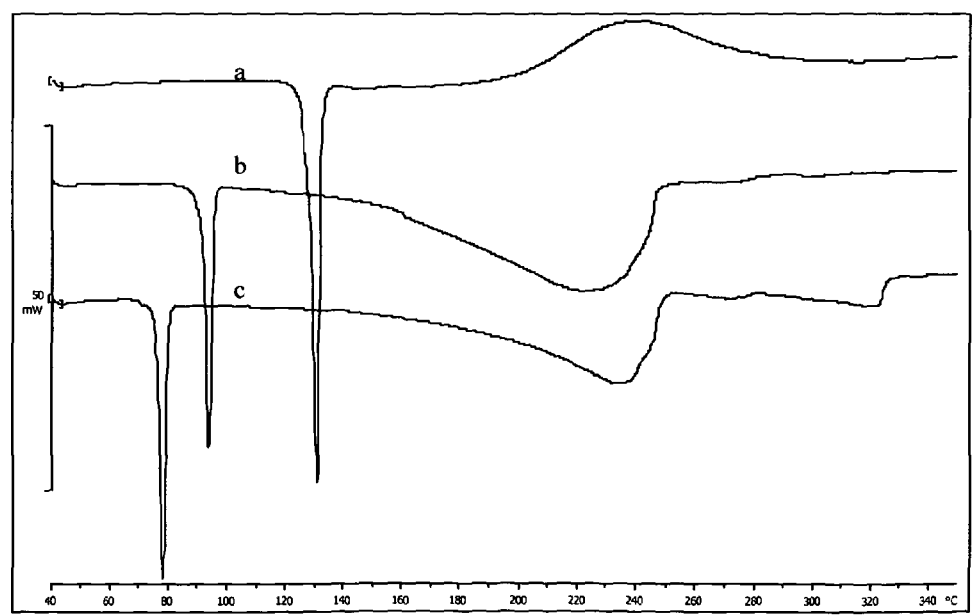
FIG. 12 shows the DSC traces of (a) 2-hydroxyimino-2-phenylacetonitrile, (b) cyprodinil-2-hydroxyimino-2-phenylacetonitrile co-crystal obtained using the technique described in Example 1a and (c) cyprodinil form B.
Figure 13:
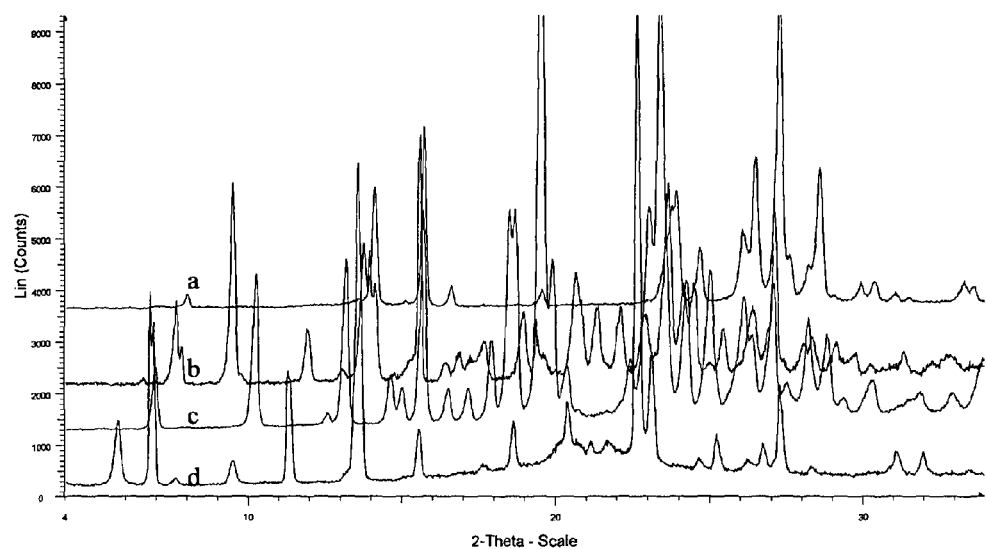
FIG. 13 shows the powder X-Ray diffraction patterns of (a) phthalimide (b) cyprodinil-phthalimide co-crystal obtained using the technique described in Example 1c, (c) cyprodinil form A and (d) cyprodinil form B.
Figure 14:
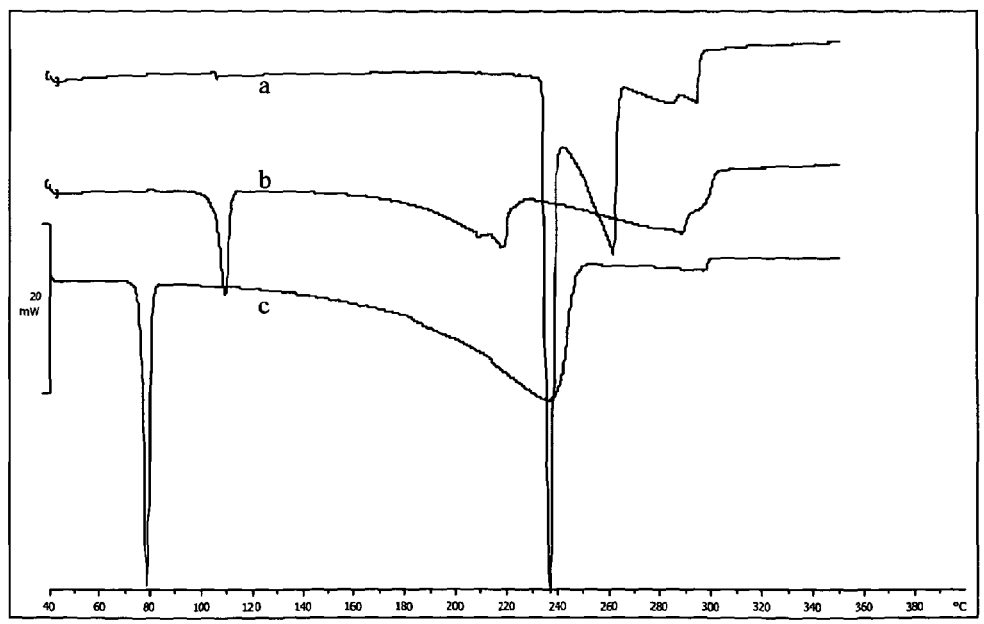
FIG. 14 shows the DSC traces of (a) phthalimide (b) cyprodinil-phthalimide co-crystal obtained using the technique described in Example 1c and (c) cyprodinil form B.

1a. Preparation of Cyprodinil Co-crystals by Cooling

Cyprodinil and a co-former (as indicated in Table 14 below) were added together to produce the correct stoichiometric mixture. The tabulated amount of solvent was added and the reaction vial was heated to 50° C. for two hours with stirring to solubilise. The mixture was then cooled to 5° C. over 5 hours and was held overnight at 5° C. Crystallised product was isolated in the morning. Analysis using PXRD and DSC confirmed co-crystallisation.

TABLE 14

| Co-former system | Mass of cyprodinil/g | Mass of Co-former/g | Stoichiometry | Solvent | Volume of solvent/ml |
|---|---|---|---|---|---|
| Pyromellitic diimide | 67 | 32.1 | 02:01 | Methanol | 450 |
| Terephthalaldehyde dioxime | 40 | 14.6 | 02:01 | Acetone | 350 |
| 2-Hydroxyimino-2-phenylacetonitrile | 1 | 0.88 | 01:01 | Acetone | 2 |

Powder X-ray diffraction patterns for the resultant crystals are shown in the figures as described above. The 2θ values of selected peak positions of the powder X-ray diffraction patterns of these crystals are shown in the tables above.

1b. Preparation of Cyprodinil Co-crystals by Microwave Irradiation

Cyprodinil (0.5 g) and dimethylglyoxime (0.13 g) were added to produce a 2:1 molar stoichiometric mixture. Acetonitrile (4 ml) was added and the resultant mixture was heated to 150° C. using microwave irradiation (300 W) for ten minutes. Crystalline product was isolated. Analysis using PXRD and DSC confirmed co-crystallisation.

1c. Preparation of Cyprodinil Co-crystals by Slurry Maturation

Cyprodinil (2.0 g) and phthalimide (1.3 g) were added to produce a 1:1 molar stoichiometric mixture. Ethanol (7.5 ml) was added and the resultant mixture was heated to 50° C. ensuring that solids remained out of solution. The mixture was stirred at 50° C. for four hours and then left for four hours at room temperature. This cycle was repeated for 7 days and then crystalline product was isolated. Analysis using PXRD and DSC confirmed co-crystallisation.

1d. Preparation of Cyprodinil Co-crystals by Evaporation

Cyprodinil (75 mg) and 2,3-naphthalenedicarboximide (68 mg) were added to produce a 1:1 molar stoichiometric mixture. Heptane (500 µl) was added and the resultant mixture was heated to 50° C. ensuring that solids remained out of solution. The mixture was stirred at 50° C. for four hours and then left for four hours at room temperature. This cycle was repeated for 7 days and then crystalline product was isolated. DMSO (250 µl) was added along with 9 mg of seed co-crystal (previously prepared by slurry maturation in heptane) and the resulting mixture was agitated at room temperature for one hour to ensure solubilisation of all components. The solution was allowed to evaporate to dryness over 1 to 2 weeks and the solid crystallised product was isolated. Analysis using PXRD confirmed co-crystallisation.

Powder X-ray diffraction patterns for the resultant crystals are shown in the figures as described above. The 2θ values of selected peak positions of the powder X-ray diffraction pattern of these crystals are shown in the tables above.

2. Stability of Cyprodinil Co-crystals

Concentrated slurries containing between 15 and 20 wt % solids of the 2:1 cyprodinil-pyromellitic diimide co-crystal and the 2:1 cyprodinil-terephthalaldehyde diioxime co-crystal were prepared in water and seeded with 1% cyprodinil and the relevant co-former. These slurries were left at 0° C. and 50° C. for a period of up to four weeks. The solids isolated from the slurries was analysed using DSC to determine whether it was present as either co-crystal or as cyprodinil+co-former.

For both co-crystals at 0° C. in a period of four weeks the solids isolated from the slurry was determined to be co-crystal. For the cyprodinil-pyromellitic diimide system at 50° C. after three weeks the solids isolated from the slurry were determined to be co-crystal. For the cyprodinil-terephthalaldehyde diioxime system at 50° C. after two weeks the solids isolated from the slurry were determined to be co-crystal. Further data at 50° C. was not collected for either system.

3. Crop Safety of Cyprodinil Co-crystals

Cyprodinil formulated as an SC300 was diluted in 200 L/ha of a 10% v/v isopropyl alcohol in water spray solution to give a final concentration of g active ingredient/ha of 2400 g/ha, 1200 g/ha, 600 g/ha, 300 g/ha and 150 g/ha. 14 days old wheat (cultivar Lona) and barley (cultivar Regina) plants were sprayed with the solution using a track sprayer. After the treatment the plants were growing in a greenhouse at 18° C. and 60% relative humidity. The phytotoxicity was evaluated visually 7 days after application, and recorded as % leaf damage per pot.

Cyprodinil-pyromellitic diimide co-crystals and cyprodinil-terephthalaldehyde diioxime co-crystals were tested in the same way.

Table 15 shows the results for cyprodinil itself and the two co-crystals:

TABLE 15

| Formulation | Cone in g ai/ha | Mean % phyto (wheat) | Mean % phyto (barley) |
|---|---|---|---|
| Cyprodinil | 2400 | 2 | |
| SC300 | 1200 | 0 | 40 |
| | 600 | 0 | 25 |
| | 300 | 0 | 11 |
| | 150 | | 3 |
| Cyprodinil-pyromellitic | 2400 | 0 | |
| diimide co-crystal | 1200 | 0 | 4 |
| SC250 | 600 | 0 | 1 |
| | 300 | 0 | 0 |
| | 150 | | 0 |
| Cyprodinil- | 2400 | 0 | |
| terephthalaldehyde | 1200 | 0 | 11 |
| diioxime co-crystal | 600 | 0 | 6 |
| SC250 | 300 | 0 | 1 |
| | 150 | | 0 |

It can clearly be seen that the two co-crystals each reduce the mean % phytotoxicity in barley plants when compared with that of the cyprodinil alone. Thus, not only does this mean that the co-crystal will allow stable SC formulations of cyprodinil to be formed, which, in itself will decrease phytotoxicity when compared to, for example, EC formulations, but, in addition, the co-crystals themselves improve inherent phytotoxicity of cyprodinil on barley.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A co-crystal comprising cyprodinil and a co-crystal forming compound selected from the group consisting of pyromellitic diimide and terephthalaldehyde diioxime;
   wherein when the co-crystal forming compound is pyromellitic diimide, the co-crystal has a powder X-ray diffraction pattern expressed in terms of 2θ angle values, wherein the powder X-ray diffraction pattern comprises at least three 2θ angle values selected from the group comprising (a) 7.3±0.2, 10.5±0.2, 11.7±0.2, 18.3±0.2, 21.4±0.2, 26.8±0.2, 28.0±0.2, and 30.2±0.2 or (b) 7.2±0.2, 10.3±0.2, 11.5±0.2, 16.4±0.2, 16.7±0.2, 19.2±0.2, 20.1±0.2, 23.6±0.2 and 23.9±0.2; and
   wherein when the co-crystal forming compound is terephthalaldehyde diioxime, the co-crystal has a powder X-ray diffraction pattern expressed in terms of 2θ angle values, wherein the powder X-ray diffraction pattern comprises at least three 2θ angle values selected from the group comprising (a) 4.4±0.2, 8.8±0.2, 11.4±0.2, 12.9±0.2, 17.7±0.2, 19.0±0.2, 19.2±0.2, 20.9±0.2, 24.4±0.2, 24.6±0.2, 25.7±0.2 and 28.7±0.2 or (b) 4.3±0.2, 8.9±0.2, 12.9±0.2, 17.6±0.2, 19.0±0.2, 19.3±0.2, 20.9±0.2, 22.3±0.2, 24.4±0.2 and 26.6±0.2.

2. The co-crystal of claim 1, wherein the co-crystal forming compound is pyromellitic diimide.

3. The co-crystal of claim 2, wherein the unit cell parameters are as shown in Table 1.

4. The co-crystal of claim 2 having a powder X-ray diffraction pattern expressed in terms of 2θ angle values, wherein the powder X-ray diffraction pattern comprises at least four 2θ angle values selected from the group comprising (a) 7.3±0.2, 10.5±0.2, 11.7±0.2, 18.3±0.2, 21.4±0.2, 26.8±0.2, 28.0±0.2, and 30.2±0.2 or (b) 7.2±0.2, 10.3±0.2, 11.5±0.2, 16.4±0.2, 16.7±0.2, 19.2±0.2, 20.1±0.2, 23.6±0.2 and 23.9±0.2.

5. The co-crystal of claim 1, wherein the co-crystal forming compound is terephthalaldehyde diioxime.

6. The co-crystal of claim 5, wherein the unit cell parameters are as shown in Table 4.

7. The co-crystal of claim 5 having a powder X-ray diffraction pattern expressed in terms of 2θ angle values, wherein the powder X-ray diffraction pattern comprises at least four 2θ angle values selected from the group comprising (a) 4.4±0.2, 8.8±0.2, 11.4±0.2, 12.9±0.2, 17.7±0.2, 19.0±0.2, 19.2±0.2, 20.9±0.2, 24.4±0.2, 24.6±0.2, 25.7±0.2 and 28.7±0.2 or (b) 4.3±0.2, 8.9±0.2, 12.9±0.2, 17.6±0.2, 19.0±0.2, 19.3±0.2, 20.9±0.2, 22.3±0.2, 24.4±0.2 and 26.6±0.2.

8. A fungicidal composition comprising the co-crystal of claim 1.

9. The composition of claim 8 which is an agrochemical composition.

10. A co-crystal comprising cyprodinil and a co-crystal forming compound selected from dimethylglyoxime and 2,3-naphthalenedicarboximide, wherein when the co-crystal forming compound is dimethylglyoxime, the co-crystal has a powder X-ray diffraction pattern expressed in terms of 2θ angle values, wherein the powder X-ray diffraction pattern comprises at least three 2θ angle values selected from the group comprising (a) 8.4±0.2, 9.6±0.2, 10.5±0.2, 12.7±0.2, 13.0±0.2, 15.8±0.2, 18.9±0.2, 20.9±0.2, 25.8±0.2 and 31.4±0.2 or (b) 8.3±0.2, 10.4±0.2, 12.8±0.2, 16.7±0.2, 16.9±0.2, 20.6±0.2, 22.2±0.2, 24.8±0.2, 25.6±0.2 and 30.9±0.2; and wherein when the co-crystal forming compound is 2,3 naphthalenedicarboximide, the co-crystal has a powder X-ray diffraction pattern expressed in terms of 2θ angle values, wherein the powder X-ray diffraction pattern comprises at least three 2θ angle values selected from the group comprising 15.3±0.2, 16.0±0.2, 19.2±0.2, 21.3±0.2, 22.0±0.2, 23.9±0.2, 24.4±0.2 and 25.4±0.2.

11. The co-crystal of claim 10, wherein the co-crystal forming compound is dimethylglyoxime and the unit cell parameters are as shown in Table 7.

12. The co-crystal of claim 11 having a powder X-ray diffraction pattern expressed in terms of 2θ angle values, wherein the powder X-ray diffraction pattern comprises at least four 2θ angle values selected from the group comprising (a) 8.4±0.2, 9.6±0.2, 10.5±0.2, 12.7±0.2, 13.0±0.2, 15.8±0.2, 18.9±0.2, 20.9±0.2, 25.8±0.2 and 31.4±0.2 or (b) 8.3±0.2, 10.4±0.2, 12.8±0.2, 16.7±0.2, 16.9±0.2, 20.6±0.2, 22.2±0.2, 24.8±0.2, 25.6±0.2 and 30.9±0.2.

13. The co-crystal of claim 10, wherein the co-crystal forming compound is 2,3-naphthalenedicarboximide.

14. The co-crystal of claim 13, wherein the unit cell parameters are as shown in Table 10.

15. The co-crystal of claim 13 having a powder X-ray diffraction pattern expressed in terms of 2θ angle values, wherein the powder X-ray diffraction pattern comprises at least four 2θ angle values selected from the group comprising 15.3±0.2, 16.0±0.2, 19.2±0.2, 21.3±0.2, 22.0±0.2, 23.9±0.2, 24.4±0.2 and 25.4±0.2.

16. A process of preparing a co-crystal of claim 1 comprising
   a) grinding, heating or contacting in solution cyprodinil with the co-crystal forming compound, under crystallisation conditions so as to form a solid phase; and
   b) isolating co-crystals comprising cyprodinil and the co-crystal forming compound.

17. A method of controlling fungal infection on plants comprising treating the plant with a fungicidally effective amount of a composition of claim 8.

* * * * *